United States Patent
Liao et al.

(10) Patent No.: US 10,179,758 B2
(45) Date of Patent: Jan. 15, 2019

(54) METHOD FOR ENHANCING UNIFORMITY OF CRYSTALLIZED SUCCINIC ACID AND PURIFIED SUCCINIC ACID PRODUCED BY THE SAME

(71) Applicant: NAN YA PLASTICS CORPORATION, Taipei (TW)

(72) Inventors: Te-Chao Liao, Taipei (TW); Jung-Jen Chuang, Taipei (TW); Cheng-Hsun Chen, Taipei (TW); Chia-Ruey Tsai, Taipei (TW); Chung-Yu Chen, Taipei (TW)

(73) Assignee: NAN YA PLASTICS CORPORATION, Taipei (TW)

( * ) Notice: Subject to any disclaimer, the term of this patent is extended or adjusted under 35 U.S.C. 154(b) by 51 days.

(21) Appl. No.: 15/615,890

(22) Filed: Jun. 7, 2017

(65) Prior Publication Data
US 2017/0362159 A1    Dec. 21, 2017

(30) Foreign Application Priority Data

Jun. 15, 2016   (TW) .................................. 105118702

(51) Int. Cl.
| | | |
|---|---|---|
| C07C 55/10 | (2006.01) | |
| B01F 7/00 | (2006.01) | |
| C07C 51/43 | (2006.01) | |
| C07C 31/02 | (2006.01) | |

(52) U.S. Cl.
CPC .......... *C07C 55/10* (2013.01); *B01F 7/00541* (2013.01); *C07C 51/43* (2013.01); *C07B 2200/13* (2013.01); *C07C 31/02* (2013.01)

(58) Field of Classification Search
None
See application file for complete search history.

(56) References Cited

U.S. PATENT DOCUMENTS

2013/0018206 A1* 1/2013 Mori ....................... C07C 51/43
562/593

* cited by examiner

*Primary Examiner* — Clinton A Brooks
(74) *Attorney, Agent, or Firm* — Bacon & Thomas, PLLC

(57) ABSTRACT

A method for crystallizing succinic acid includes agitating a succinic acid reaction solution with a jet-flow agitator that is rotated at low speed and has a low volume power density; compared with the conventional agitators, the jet-flow agitator helps increase the uniformity of succinic acid particles, shorten the time required for crystallizing succinic acid, and raise the yield of the crystallized succinic acid as well as purity of crystallized succinic acid having a purity of 99.8-99.9%.

6 Claims, 3 Drawing Sheets

METHOD FOR ENHANCING UNIFORMITY OF CRYSTALLIZED SUCCINIC ACID AND PURIFIED SUCCINIC ACID PRODUCED BY THE SAME

BACKGROUND OF THE INVENTION

1. Field of the Invention

The present invention relates to a method for producing, and enhancing the uniformity of, crystallized succinic acid. More particularly, the invention relates to a method for dispersing succinic acid crystals homogeneously under a low-rotation-speed and low-power-consumption condition, thereby increasing the yield and purity of the succinic acid product.

2. Description of Related Art

Conventionally, succinic acid (SA) can be produced by any of the following methods:
1. Oxidation Method:
Paraffin wax is subjected to an advanced oxidation process to form a mixture of various carboxylic acids. The mixture is then separated by distillation and crystallization to produce succinic acid.
2. Hydrogenation Method:
Maleic anhydride or trans-butenedioic acid goes through a hydrogenation process under the action of a catalyst to produce succinic acid, which is subsequently separated as the end product. The catalyst, either nickel or a noble metal, has a reaction temperature of about 130-140° C.
3. Electrolysis Method:
Maleic anhydride is dissolved in water to produce maleic acid. The maleic acid is reduced such that each hydrogen ion ($H^+$) receives an electron from the anode to become a hydrogen atom. Then, an addition reaction takes place between the hydrogen atoms and the maleic acid to yield succinic acid.

The aforesaid conventional methods for producing succinic acid, however, are disadvantageous that both a cooling process and a crystallization process are required in the course of producing the succinic acid product. Firstly, the crystallization reaction is time-consuming and uses up considerable power from about 400 to about 3000 $W/m^3$. Secondly, the equipment for producing succinic acid is expensive and is difficult to operate and maintain. Last but not least, the succinic acid product is not uniform in terms of crystal size and consequently has a low yield and low purity.

SUMMARY OF THE INVENTION

In order to overcome the aforesaid drawbacks of the prior art regarding in low uniformity in size of succinic acid crystals as well as in high power consumption required for the crystallization process, a primary objective of the present invention is to disclose a method for enhancing uniformity of crystallized succinic acid, whose manufacturing method is utilized with a crystallization tank having a jet-flow agitator mounted inside and rotated at low speed to allow the crystallized succinic acid to be produced at a low-power-consumption condition.

More specifically, the jet-flow agitator creates a double disturbance effect by providing both a rotary stir and jet flows to a reaction solution already poured into the crystallization tank. As a result, turbulent flows are generated in the reaction solution and disperse succinic acid solids uniformly in the reaction solution to enable sufficient crystallization and purification, thereby increasing the uniformity of crystallized succinic acid, shortening the time required for succinic acid crystallization, and raising the yield and purity of crystallized succinic acid. The succinic acid thus obtained has a purity of 99.8-99.9%.

In order to make a breakthrough for the conventional methods for producing succinic acid, another objective of the present invention is to disclose a novel method for producing succinic acid that can enhance uniformity of crystallized succinic acid at a low-power-consumption environment, which method comprises the steps of:
a) preparing a crystallization tank containing therein a jet-flow agitator composed of a rotating shaft and a plurality of inclined converging-tube blades, and the rotating shaft is configured to drive the inclined converging-tube blades into rotation;
b) pouring a solution into the crystallization tank of the step a), wherein the solution is one selected from the group consisting of water, methanol and ethanol;
c) adding succinic acid solids into the solvent to form a reaction solution by a weight ratio of the solvent to the succinic acid solids ranging from 2.0 to 10.0;
d) activating the jet-flow agitator of the step a) to drive the inclined converging-tube blades of the jet-flow agitator rotating at 50-500 rpm to disturb the reaction solution of the step c) by both a rotary stir and jet flows, i.e., to allow the reaction solution of the step c) undergoes irregular fluctuations or mixing through turbulent flows, and thereby dispersing the succinic acid solids uniformly in the reaction solution;
e) setting a cooling rate of the crystallization tank to 10-35° C. per hour, and allowing the reaction solution of the step d) to undergo a crystallization and purification reaction for 1-8 hours at a reaction pressure of 5-100 lbf/in2 and a reaction temperature of 0-90° C. such that the succinic acid solids in the reaction solution are crystallized and purified to form high-purity succinic acids; and
f) filtering out and removing the solvent from the reaction solution of the step e) to obtain a solid residue, after the crystallization and purification reaction of step e) is completed, and drying the solid residue to obtain the high-purity succinic acid.

The disclosed method for enhancing uniformity of crystallized succinic acid has the following advantageous effects:
1. A reaction solution containing a high concentration of succinic acid solids is agitated at a low-rotation-speed and low-power-consumption environment by a jet-flow agitator whose stirring action and jet flows create a double disturbance effect and which, therefore, suspends the succinic acid solids uniformly in the reaction solution. The method of the present invention thus increases the efficiency of mixing the succinic acid solids with the solvent of the reaction solution to accelerate crystallization and purification, thereby raising the yield and purity of the succinic acid product substantially.
2. With the jet-flow agitator performing succinic acid crystallization and purification at a low-rotation-speed and low-power-consumption environment, in addition to the reaction time is shortened by 25-30%, the power consumed by the crystallization reaction per unit volume (also referred to herein as the volume power density) is substantially reduced to 115-190 $W/m^3$, if compared with the volume power density of 250-650 $W/m^3$ required for a conventional agitator used for performing the same procedures, the volume power density consumed is obviously saved by 24-80% due to decreasing from the 250-650 W/m$^3$ to 115-190 W/m$^3$. Thus, the method of the present invention contributes to a significant reduction in production cost.

DETAILED DESCRIPTION OF THE INVENTION

Figure 1:
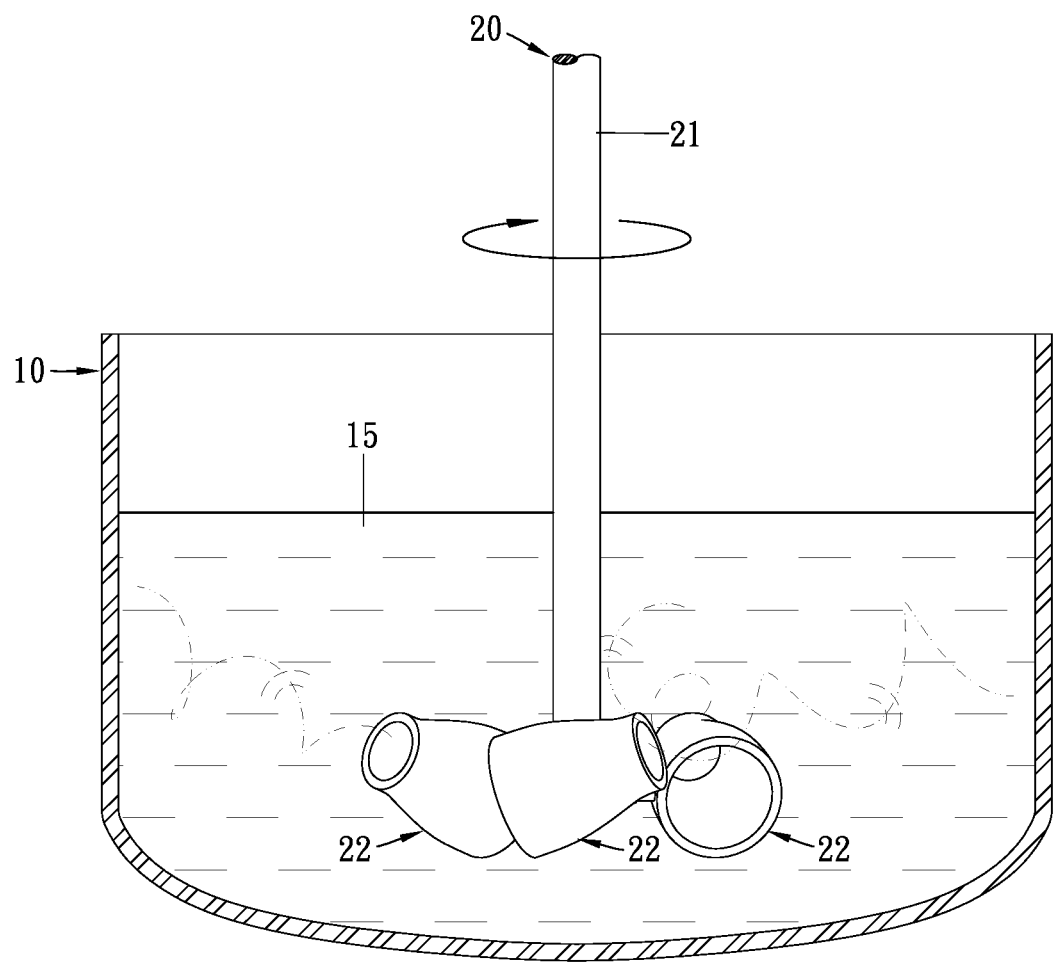
FIG. 1 schematically shows a succinic acid crystallization tank for use in the present invention, and how turbulent flows are generated in a reaction solution by a jet-flow agitator at a low-power-consumption environment.

According to the present invention, a method for producing succinic acid is performed as follows. Referring to FIG. 1, a reaction solution 15 containing succinic acid solids and a solvent is poured into a crystallization tank 10, where crystallization and purification of succinic acid are carried out under a predetermined reaction pressure and reaction temperature.

The crystallization tank 10 is provided therein with a jet-flow agitator 20, which is composed of a rotating shaft 21 and a plurality of inclined converging-tube blades 22 provided at an end of the rotating shaft 21.

The rotating shaft 21 of the jet-flow agitator 20 is connected to the driving shaft of a motor (not shown in drawings) by a belt- or gear-based transmission mechanism. The motor drives the rotating shaft 21 of the jet-flow agitator 20 into rotation, and consequently the inclined converging-tube blades 22 are followed to make a rotation synchronously to agitate the reaction solution 15 through turbulent flows to undergo irregular fluctuations or mixing.

More specifically, when the reaction solution 15 is agitated by the inclined converging-tube blades 22 for agitation, a double disturbance effect consisting of a rotary stir and inclined jet flows, by generation from the inclined converging-tube blades 22 in rotation, is applied to the reaction solution 15 (containing succinic acid solids) in the crystallization tank 10, thereby to disperse the succinic acid solids uniformly in the reaction solution 15 to facilitate crystallization and purification.

Preferably, the crystallization tank 10 is a barrel-shaped container, and the ratio of the height to the inner diameter of the barrel-shaped container ranges from 0.4 to 3. Moreover, in addition to containing therein the jet-flow agitator 20, the crystallization tank 10 may be optionally provided with a heat exchanger plate or a coil condenser to prevent heat accumulation, or more particularly to remove in time, through the additional heat exchange function, the heat released from the succinic acid crystallization reaction.

Figure 3:
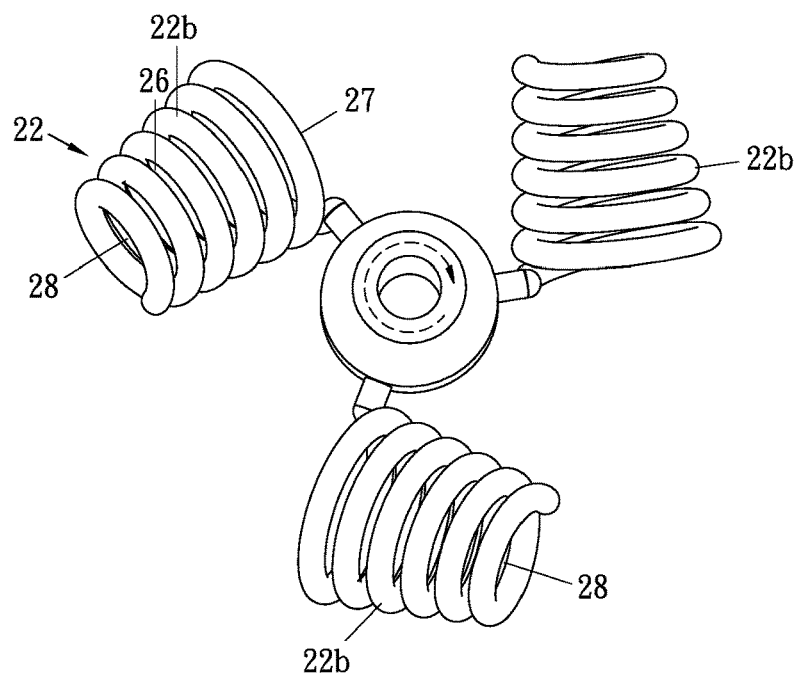
FIG. 3 schematically shows an inclined conical spring impeller (with inclined conical spring blades) for use by the jet-flow agitator in FIG. 1.
Figure 2:
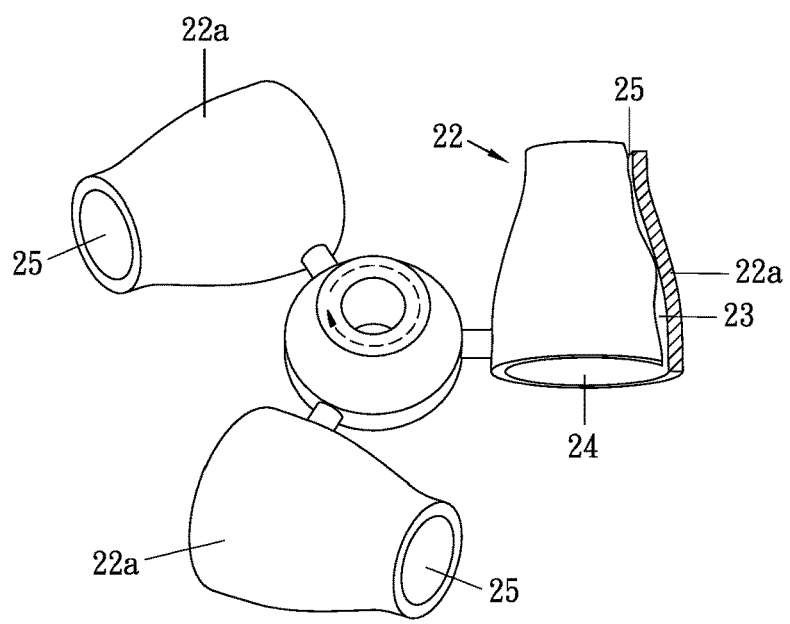
FIG. 2 schematically shows an inclined nozzle impeller (with inclined nozzle blades) for use by the jet-flow agitator in FIG. 1.

As shown in FIG. 1 through FIG. 3, the inclined converging-tube blades 22 of the jet-flow agitator 20 are configured for providing with a double disturbance effect as aforesaid having both a rotary stir and an inclined jet flows simultaneously. The inclined converging-tube blades 22 may be structured as either inclined nozzle blades 22a shown in FIG. 2 or inclined conical spring blades 22b shown in FIG. 3.

As shown in FIG. 1 and FIG. 2, each inclined nozzle blade 22a has a hollow tubular structure including a turbulent-flow channel 23, a liquid inlet end 24, and a jet-flow end 25. The turbulent-flow channel 23 is formed inside the hollow tubular structure and has a decreasing channel diameter. The liquid inlet end 24 and the jet-flow end 25 are formed at the two end openings of the turbulent-flow channel 23 respectively. More specifically, the liquid inlet end 24 is formed at the greater-diameter end of the turbulent-flow channel 23, and the jet-flow end 25 is formed at the smaller-diameter end of the turbulent-flow channel 23. In terms of elevation, the jet-flow end 25 of the turbulent-flow channel 23 is higher than the liquid inlet end 24 of the turbulent-flow channel 23 such that the turbulent-flow channel 23 and the jet-flow end 25 are tilted upward.

Similarly, referring to FIG. 3, each inclined conical spring blade 22b has a spiral spring-shaped tubular structure including a turbulent-flow channel 26, a liquid inlet end 27, and a jet-flow end 28. The turbulent-flow channel 26 is enclosed by the spiral spring-shaped tubular body and has a decreasing channel diameter. The liquid inlet end 27 and the jet-flow end 28 are formed at the two end openings of the turbulent-flow channel 26 respectively. More specifically, the liquid inlet end 27 is formed at the larger-diameter end of the turbulent-flow channel 26, and the jet-flow end 28 is formed at the smaller-diameter end of the turbulent-flow channel 26. In terms of elevation, the jet-flow end 28 of the turbulent-flow channel 26 is higher than the liquid inlet end 27 of the turbulent-flow channel 26 such that the turbulent-flow channel 26 and the jet-flow end 28 are tilted upward.

Unless otherwise specified, all the functions described below as pertaining to the inclined nozzle blades 22a are shared by the inclined conical spring blades 22b.

Referring to FIG. 1 to FIG. 3, when the motor drives the inclined nozzle blades 22a of the jet-flow agitator 20 to rotate, the reaction solution 15 containing succinic acid solids is rotationally stirred by the inclined nozzle blades 22a in a periodic manner. Meanwhile, the reaction solution 15 keeps flowing into the turbulent-flow channel 23 of each inclined nozzle blade 22a through the corresponding liquid inlet end 24, is driven toward the corresponding jet-flow end 25 under the guidance of the tapered turbulent-flow channel 23, and eventually spurts out in a slantingly upward direction. As the reaction solution 15 containing succinic acid solids is rotationally stirred at the same time, the combination of the rotary stir and the inclined jet flows produces a double disturbance effect that causes turbulent flows in the reaction solution 15, thereby dispersing the succinic acid solids uniformly in the reaction solution 15.

It should be pointed out that the jet-flow agitator 20 of the present invention only has to rotate at low speed, and turbulent flows will be generated in the reaction solution 15 to promote uniform dispersion and sufficient crystallization and purification of the succinic acid solids in the reaction solution 15.

As shown in FIG. 2 and FIG. 3, the inclined conical spring blades 22b are different from the inclined nozzle blades 22a mainly in that the turbulent-flow channel 26 of each inclined conical spring blade 22b is in communication with the space outside the inclined conical spring blade 22b through the gaps between the conical spring-shaped tubular structure, as well as with the liquid inlet end 27 and the jet-flow end 28 at the two ends of the turbulent-flow channel 26.

When the motor drives the inclined conical spring blades 22b of the jet-flow agitator 20 of the present invention into rotation, the reaction solution 15 entering the turbulent-flow channel 26 of each inclined conical spring blade 22b spurts not only from the corresponding jet-flow end 28, but also from the gaps between the conical spring-shaped tubular structure of the inclined conical spring blades 22b. This phenomenon causes even more disturbance to, and hence more vehement turbulent flows in, the reaction solution 15 containing succinic acid solids, and is therefore more effective in promoting uniform dispersion and sufficient crystallization and purification of the succinic acid solids in the reaction solution 15.

It can be known from the above that the jet-flow agitator 20 of the present invention can better stir high-viscosity reaction solutions when equipped with the inclined conical spring blades 22b as its stirring blades.

Figure 4:
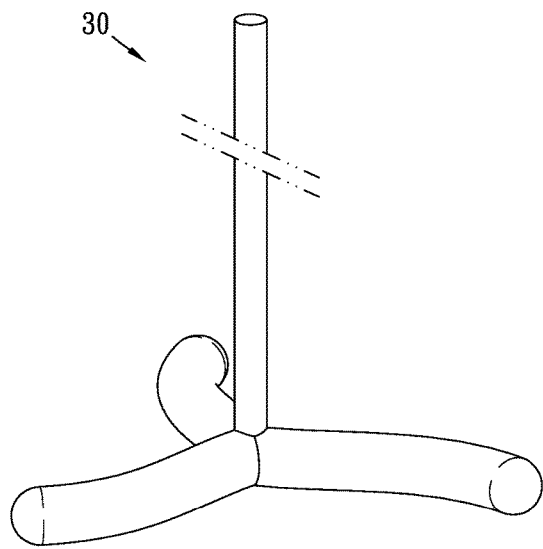
FIG. 4 schematically shows a retreat curve impeller for use by a conventional agitator.
Figure 5:
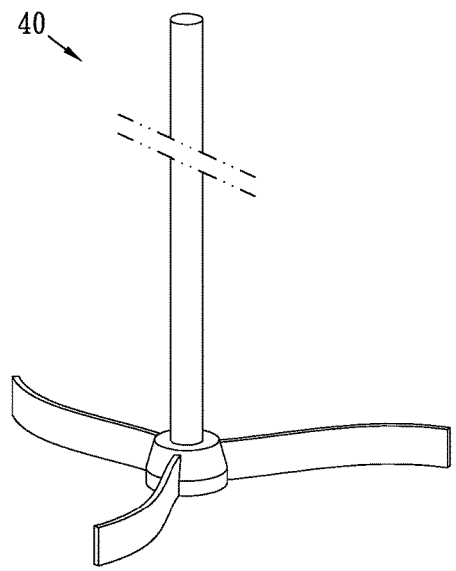
FIG. 5 schematically shows a curved blade impeller for use by a conventional agitator.
Figure 6:
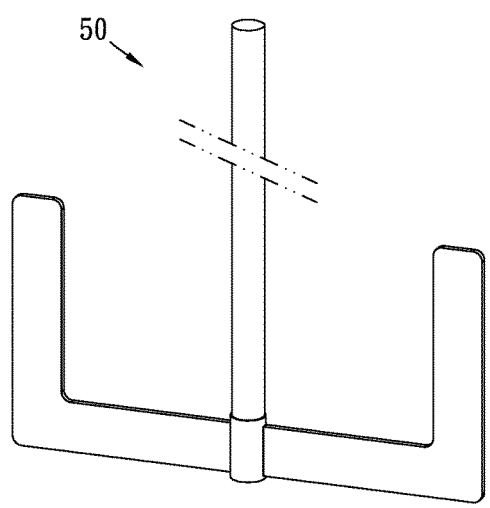
FIG. 6 schematically shows an anchor impeller for use by a conventional agitator.

By contrast, if the reaction solution 15 containing succinic acid solids is agitated with a conventional agitator equipped with a retreat curve impeller 30 as shown in FIG. 4, a curved blade impeller 40 as shown in FIG. 5, or an anchor impeller 50 as shown in FIG. 6, the lack of jet flows will leave the reaction solution 15 to a periodic rotary stir only. And without turbulent flows in the reaction solution 15, the succinic acid solids will be dispersed in the reaction solution 15 in a non-uniform manner.

According to the method of the present invention for producing succinic acid, crystallization and purification of succinic acid are carried out via the jet-flow agitator 20 of the present invention in the crystallization tank 10, with a reaction temperature of 0-90° C., preferably 20-80° C., a reaction pressure of 5-100 lbf/in$^2$, and a crystallization reaction time for 1-8 hours. Compared with the prior art, the method of the present invention for producing succinic acid shortens the time required for the crystallization reaction of succinic acid and can increase the yield and purity of crystallized succinic acid.

To raise the purity of crystallized succinic acid to 99.8-99.99%, the composition of the reaction solution 15 containing succinic acid solids of the present invention follows a weight ratio of the solvent to the succinic acid solids ranging from 2.0 to 10.0, preferably ranging from 2.3 to 7.0, more preferably ranging from 4.0 to 7.0, most preferably equivalent to 4.

The solvent may be selected from water, methanol and ethanol, and is preferably ethanol. Once reacting with the succinic acid solids, the aforesaid solvents help increase the purity of crystallized succinic acid without producing side products or having adverse effects on the crystallization speed of succinic acid.

Based on the foregoing description, and referring to FIG. 1, the method disclosed herein for enhancing the uniformity of crystallized succinic acid and shortening the reaction time comprises the steps of:

a) preparing a crystallization tank 10 containing therein a jet-flow agitator 20;
  The jet-flow agitator 20 is composed of a rotating shaft 21 and a plurality of inclined converging-tube blades 22 driven by the rotating shaft 21 into rotation.

b) pouring a solvent into the crystallization tank 10 of the step a);
  The solvent is one selected from the group consisting of water, methanol and ethanol.

c) adding succinic acid solids to the solvent of the step b) to form a reaction solution 15 by according to a weight ratio of the solvent to the succinic acid solids ranging from 2.0 to 10.0; preferably ranging from 2.3 to 7.0, more preferably ranging from 4.0 to 7.0, most preferably equivalent to 4;

d) activating the jet-flow agitator 20 of the step a) to have the inclined converging-tube blades 22 thereof rotated at 50-500 rpm to disperse the succinic acid solids uniformly in the reaction solution 15;
  The inclined converging-tube blades 22 of the jet-flow agitator 20 is rotated at a low-rotation-speed to disturb and agitate the reaction solution 15 of the step c) by both a rotary stir and jet flows to cause the reaction solution 15 to undergo irregular fluctuations or mixing through turbulent flows in the reaction solution 15 and thereby to disperse the succinic acid solids uniformly in the reaction solution 15.

e) setting a cooling rate of the crystallization tank 10 to 10-35° C. per hour, and allowing the reaction solution of the step d) to undergo a crystallization and purification reaction for 1-8 hours at a reaction pressure of 5-100 lbf/in$^2$ and a reaction temperature of 0-90° C. such that the succinic acid solids in the reaction solution 15 are crystallized and are further purified to form high-purity succinic acid; and f) filtering out and removing the solvent from the reaction solution 15 of the step e) to obtain a solid residue, after the crystallization and purification reaction of step e) is completed, and drying the solid residue to obtain the high-purity succinic acid.

EXAMPLES AND COMPARATIVE EXAMPLES

To illustrate the features of the disclosed method for producing succinic acid, the following examples 1-5 and comparative examples 1-8 are provided, using different agitators in the succinic acid crystallization tank. The agitators used in the crystallization tank in examples 1-5 and comparative examples 1-8 are tabulated as follows:

| Agitator in crystallization tank | Impeller/Stirring blades | | Reference drawing |
|---|---|---|---|
| Examples 1, 3-5 | Jet-flow agitator | Inclined nozzle impeller (with inclined nozzle blades 22a) | FIG. 2 |
| Example 2 | Jet-flow agitator | Inclined conical spring impeller (with inclined conical spring blades 22b) | FIG. 3 |
| Comparative examples 1, 2 | Conventional agitator | Retreat curve impeller 30 | FIG. 4 |
| Comparative examples 3, 4 | Conventional agitator | Curved blade impeller 40 | FIG. 5 |
| Comparative examples 5, 6 | Conventional agitator | Anchor impeller 50 | FIG. 6 |
| Comparative examples 7, 8 | Jet-flow agitator | Inclined nozzle impeller (with inclined nozzle blades 22a) | FIG. 2 |

The succinic acid product of each example and comparative example was assessed by the following testing methods, using the measurement equipment specified:

1. Volume power density (unit: Watt/m$^3$ or W/m$^3$):
  The power consumed per unit volume was measured with Phase Difference Torque Detector TH2000, manufactured by Ono Sokki of Japan, and can be expressed by the equation:

Volume power density $Q = T*(2n\pi/60)/V$, where T is torque (Nm), n is rotation speed (rpm), and V is the volume (m$^3$) of succinic acid reaction solution.

2. Average particle size and particle size (distribution) uniformity:

Particle size ranges $D_{10}$, $D_{50}$, and $D_{90}$ were determined with Laser Diffraction Particle Size Analyzer LS230, manufactured by Beckman Coulter of USA. $D_{50}$ (μm) was used to represent the average particle size, or mass median diameter, of any given sample.

Particle size uniformity (or particle size distribution uniformity) is the ratio of $(D_{90}-D_{10})/D_{50}$. The smaller the value of particle size uniformity, the more uniformly the particles are distributed in a given sample.

Example 1

14700 g of water, serving as a solvent, was poured into a crystallization tank, whose volume is 30 L, followed by 6300 g of succinic acid solids, which mixed with the water to form a succinic acid reaction solution. A jet-flow agitator, equipped with an inclined nozzle impeller, was then activated to stir the succinic acid reaction solution. With the jet-flow agitator rotating at 330 rpm, the succinic acid solids were completely suspended in the water. The volume power density corresponding to the jet-flow agitator rotating at 330 rpm was determined as 184 W/m³.

Following that, under the preset pressure of 50 lbf/in² and by means of a cooling circulator, the succinic acid reaction solution was heated to 80° C. and stirred. After 20 minutes of stirring, the reaction solution was cooled down from 80° C. to 5° C. at a cooling rate of 30° C. per hour and then kept at the same temperature for one hour. Once the 2.5-hour reaction was completed, the reaction solution was cooled down to room temperature, and the solvent was removed by filtration. After drying, a high-purity succinic acid product was obtained.

The test results of the succinic acid product are shown in Table 1: the yield of crystallized succinic acid was 99.1%, purity was 99.9%, average particle size $D_{50}$ was 580 μm, and particle size uniformity was 2.06.

Example 2

The production method of example 1 remained except that 5250 g of succinic acid solids and 15800 g of water serving as a solvent were used instead, and that the jet-flow agitator was equipped with an inclined conical spring impeller for stirring the succinic acid reaction solution.

With the jet-flow agitator rotating at 300 rpm, the succinic acid solids were completely suspended in the water. The volume power density corresponding to the jet-flow agitator rotating at 300 rpm was determined as 138 W/m³. After the 2.5-hour reaction, the succinic acid product obtained was tested and produced the results in Table 1: the yield of crystallized succinic acid was 98.9%, purity was 99.8%, average particle size $D_{50}$ was 564 μm, and particle size uniformity was 2.15.

Example 3

The production method of example 1 remained except that 4200 g of succinic acid solids and 16800 g of water serving as a solvent were used instead, and that the reaction solution was cooled down from 70° C. to 5° C.

With the jet-flow agitator rotating at 286 rpm, the succinic acid solids were completely suspended in the water. The volume power density corresponding to the jet-flow agitator rotating at 286 rpm was determined as 120 W/m³. After the 2.5-hour reaction, the succinic acid product obtained was tested and produced the results in Table 1: the yield of crystallized succinic acid was 99.3%, purity was 99.8%, average particle size $D_{50}$ was 605 μm, and particle size uniformity was 1.84.

Example 4

The production method of example 1 remained except that 2630 g of succinic acid solids and 18400 g of water serving as a solvent were used instead.

With the jet-flow agitator rotating at 282 rpm, the succinic acid solids were completely suspended in the water. The volume power density corresponding to the jet-flow agitator rotating at 282 rpm was determined as 116 W/m³. After the 2.5-hour reaction, the succinic acid product obtained was tested and produced the results in Table 1: the yield of crystallized succinic acid was 99.2%, purity was 99.8%, average particle size $D_{50}$ was 680 μm, and particle size uniformity was 1.96.

Example 5

The production method of example 4 remained except that the solvent was changed to ethanol.

With the jet-flow agitator rotating at 280 rpm, the succinic acid solids were completely suspended in the ethanol. The volume power density corresponding to the jet-flow agitator rotating at 280 rpm was determined as 115 W/m³. After the 2.5-hour reaction, the succinic acid product obtained was tested and produced the results in Table 1: the yield of crystallized succinic acid was 99.3%, purity was 99.9%, average particle size $D_{50}$ was 685 μm, and particle size uniformity was 1.90.

Comparative Example 1

The production method of example 1 remained except that a conventional agitator equipped with a retreat curve impeller manufactured by Pfaudler was used to stir the succinic acid reaction solution, and that the cooling rate of the reaction solution was changed to 20° C. per hour.

With the conventional agitator rotating at 480 rpm, the succinic acid solids were suspended in the water. The volume power density corresponding to the conventional agitator rotating at 480 rpm was determined as 420 W/m³. After the 3.5-hour reaction, the succinic acid product obtained was tested and produced the results in Table 1: the yield of crystallized succinic acid was 93.1%, purity was 99.3%, average particle size $D_{50}$ was 465 μm, and particle size uniformity was 2.50.

Comparative Example 2

The production method of example 2 remained except that a conventional agitator equipped with a retreat curve impeller manufactured by Pfaudler was used to stir the succinic acid reaction solution, and that the cooling rate of the reaction solution was changed to 20° C. per hour.

With the conventional agitator rotating at 425 rpm, the succinic acid solids were suspended in the water. The volume power density corresponding to the conventional agitator rotating at 425 rpm was determined as 296 W/m³. After the 3.5-hour reaction, the succinic acid product obtained was tested and produced the results in Table 1: the yield of crystallized succinic acid was 93.8%, purity was 99.1%, average particle size $D_{50}$ was 440 μm, and particle size uniformity was 2.47.

Comparative Example 3

The production method of example 1 remained except that a conventional agitator equipped with a curved blade impeller manufactured by Pfaudler was used to stir the succinic acid reaction solution, and that the cooling rate of the reaction solution was changed to 20° C. per hour.

With the conventional agitator rotating at 400 rpm, the succinic acid solids were suspended in the water. The volume power density corresponding to the conventional agitator rotating at 400 rpm was determined as 625 W/m$^3$. After the 3.5-hour reaction, the succinic acid product obtained was tested and produced the results in Table 1: the yield of crystallized succinic acid was 94.2%, purity was 99.3%, average particle size $D_{50}$ was 472 μm, and particle size uniformity was 2.56.

Comparative Example 4

The production method of example 2 remained except that a conventional agitator equipped with a curved blade impeller manufactured by Pfaudler was used to stir the succinic acid reaction solution, and that the cooling rate of the reaction solution was changed to 20° C. per hour.

With the conventional agitator rotating at 350 rpm, the succinic acid solids were suspended in the water. The volume power density corresponding to the conventional agitator rotating at 350 rpm was determined as 419 W/m$^3$. After the 3.5-hour reaction, the succinic acid product obtained was tested and produced the results in Table 1: the yield of crystallized succinic acid was 93.5%, purity was 99.5%, average particle size $D_{50}$ was 486 μm, and particle size uniformity was 2.61.

Comparative Example 5

The production method of example 1 remained except that a conventional agitator equipped with an anchor impeller manufactured by Pfaudler was used to stir the succinic acid reaction solution, and that the cooling rate of the reaction solution was changed to 20° C. per hour.

With the conventional agitator rotating at 220 rpm, the succinic acid solids were suspended in the water. The volume power density corresponding to the conventional agitator rotating at 220 rpm was determined as 589 W/m$^3$. After the 3.5-hour reaction, the succinic acid product obtained was tested and produced the results in Table 1: the yield of crystallized succinic acid was 94.6%, purity was 99.1%, average particle size $D_{50}$ was 498 μm, and particle size uniformity was 2.42.

Comparative Example 6

The production method of example 2 remained except that a conventional agitator equipped with an anchor impeller manufactured by Pfaudler was used to stir the succinic acid reaction solution, and that the cooling rate of the reaction solution was changed to 20° C. per hour.

With the conventional agitator rotating at 200 rpm, the succinic acid solids were suspended in the water. The volume power density corresponding to the conventional agitator rotating at 200 rpm was determined as 421 W/m$^3$. After the 3.5-hour reaction, the succinic acid product obtained was tested and produced the results in Table 1: the yield of crystallized succinic acid was 94.9%, purity was 99.4%, average particle size $D_{50}$ was 508 μm, and particle size uniformity was 2.63.

Comparative Example 7

The production method of example 1 remained except that 2630 g of succinic acid solids was dissolved in 32800 g of water, which served as a solvent and was far more than that used in example 1.

With the jet-flow agitator rotating at 270 rpm, the succinic acid solids were completely suspended in the water. The volume power density corresponding to the jet-flow agitator rotating at 270 rpm was determined as 111 W/m$^3$. After the 2.5-hour reaction, the succinic acid product obtained was tested and produced the results in Table 1: the yield of crystallized succinic acid was 96.8%, purity was 99.5%, average particle size $D_{50}$ was 520 μm, and particle size uniformity was 2.28.

Comparative Example 8

The production method of example 1 remained except that 2630 g of succinic acid solids was dissolved in 4800 g of water, which served as a solvent and was far less than that used in example 1.

With the jet-flow agitator rotating at 350 rpm, the succinic acid solids were completely suspended in the water. The volume power density corresponding to the jet-flow agitator rotating at 350 rpm was determined as 144 W/m$^3$. After the 2.5-hour reaction, the succinic acid product obtained was tested and produced the results in Table 1: the yield of crystallized succinic acid was 96.5%, purity was 99.4%, average particle size $D_{50}$ was 518 μm, and particle size uniformity was 2.32.

TABLE 1

Stirring power test by crystallizing succinic acid, and some relevant parameters of crystallization

| | | Examples | | | | | Comparative Examples | | | | | | | |
|---|---|---|---|---|---|---|---|---|---|---|---|---|---|---|
| | | 1 | 2 | 3 | 4 | 5 | 1 | 2 | 3 | 4 | 5 | 6 | 7 | 8 |
| Impeller of agitator and Speed | Inclined nozzle impeller | ✓ | | ✓ | ✓ | ✓ | | | | | | | ✓ | ✓ |
| | Inclined conical spring impeller | | ✓ | | | | | | | | | | | |
| | Retreat curve impeller | | | | | | ✓ | ✓ | | | | | | |
| | Curved blade impeller | | | | | | | | ✓ | ✓ | | | | |

TABLE 1-continued

Stirring power test by crystallizing succinic acid, and some relevant parameters of crystallization

| | | Examples | | | | | Comparative Examples | | | | | | | |
|---|---|---|---|---|---|---|---|---|---|---|---|---|---|---|
| | | 1 | 2 | 3 | 4 | 5 | 1 | 2 | 3 | 4 | 5 | 6 | 7 | 8 |
| | Anchor impeller | | | | | | | | | | ✓ | ✓ | | |
| | Revolutions per minute (rpm) | 330 | 300 | 286 | 282 | 280 | 480 | 425 | 400 | 350 | 220 | 200 | 270 | 350 |
| Reaction solution | Succinic acid (kg) | 6.30 | 5.25 | 4.20 | 2.63 | 2.63 | 6.30 | 5.25 | 6.30 | 5.25 | 6.30 | 5.25 | 2.63 | 2.63 |
| | Water solvent (kg) | 14.7 | 15.8 | 16.8 | 18.4 | — | 14.7 | 15.8 | 14.7 | 15.8 | 14.7 | 15.8 | 32.8 | 4.8 |
| | Ethanol solvent (kg) | — | — | — | — | 18.4 | — | — | — | — | — | — | — | — |
| Ratio of solvent to succinic acid | | 2.33 | 3.0 | 4.0 | 7.02 | 7.02 | 2.33 | 3.0 | 2.33 | 3.0 | 2.33 | 3.0 | 12.5 | 1.83 |
| Ratio of succinic acid to solvent (%) | | 42.9 | 33.2 | 25.0 | 14.2 | 14.2 | 42.9 | 33.2 | 42.9 | 33.2 | 42.9 | 33.2 | 8.0 | 54.8 |
| Reaction time (hr) | | 2.5 | 2.5 | 2.5 | 2.5 | 2.5 | 3.5 | 3.5 | 3.5 | 3.5 | 3.5 | 3.5 | 2.5 | 2.5 |
| Yield of crystallized succinic acid (%) | | 99.1 | 98.9 | 99.3 | 99.2 | 99.3 | 93.1 | 93.8 | 94.2 | 93.5 | 94.6 | 94.9 | 96.8 | 96.5 |
| Volume power density (W/m$^3$) | | 184 | 138 | 120 | 116 | 115 | 420 | 296 | 625 | 419 | 589 | 421 | 111 | 144 |
| Mass median diameter (μm) | | 580 | 564 | 605 | 680 | 685 | 465 | 440 | 472 | 486 | 498 | 508 | 520 | 518 |
| Particle size distribution[1] | | 2.06 | 2.15 | 1.84 | 1.96 | 1.90 | 2.50 | 2.47 | 2.56 | 2.61 | 2.42 | 2.63 | 2.28 | 2.32 |
| Purity (%) | | 99.9 | 99.8 | 99.8 | 99.8 | 99.9 | 99.3 | 99.1 | 99.3 | 99.5 | 99.1 | 99.4 | 99.5 | 99.4 | note #:
[1]The smaller value of particle size distribution holds, the better for the tested sample is.

Results:

1. In examples 1-5, the weight ratio of the solvent (water or ethanol) to the succinic acid solids ranged from 2.33 to 7.02, and with the jet-flow agitator stirring each succinic acid reaction solution at a low rotation speed ranged from 280 rpm to 330 rpm) and a low volume power density ranged from 115 W/m$^3$ to 184 W/m$^3$, the time required for crystallizing succinic acid was one hour shorter than that of comparative examples 1-6.

Moreover, according to the test results of examples 1-5 as shown in Table 1, the yield of crystallized succinic acid reached 98.9-99.3%, purity reached 99.8-99.9%, and particle size uniformity reached 1.84-2.15, all of which results are significantly better than those of comparative examples 1-6, in which a conventional agitator was used to produce succinic acid.

In particular, the uniformity of succinic acid crystals was effectively enhanced in examples 1-5.

2. In comparative examples 7 and 8, the weight ratio of the solvent (water or ethanol) to the succinic acid solids was 12.5 and 1.83 respectively, as opposed to the weight ratio ranged from 2.33 to 7.02 of examples 1-5. According to Table 1, the test results of examples 1-5 were significantly better than those of comparative examples 7 and 8 in terms of yield, purity, and particle size uniformity of crystallized succinic acid.

This demonstrates that the weight ratio of the solvent (water or ethanol) to the succinic acid solids ranged from 2.33 to 7.02 in examples 1-5 were indeed effective in enhancing the uniformity of succinic acid crystals.

3. In examples 3-5, the weight ratio of the solvent (water or ethanol) to the succinic acid solids ranged from 4.0 to 7.02. According to Table 1, the test results of examples 3-5 (including the yield of crystallized succinic acid, which was as high as 99.2-99.3%; volume power density corresponding to the jet-flow agitator, which was merely 115-120 W/m$^3$; and particle size uniformity of crystallized succinic acid, which ranged from 1.84 to 1.96) were significantly better than those of the other examples and all the comparative examples.

4. In example 3, the weight ratio of the solvent (water) to the succinic acid solids was 4.0. According to Table 1, particle size uniformity of the crystallized succinic acid of this example was the lowest value of 1.84, hence the best, of all the examples and comparative examples.

5. Examples 4 and 5 used the same amount of solvent, the same amount of succinic acid solids, but different types of solvent (water and ethanol, respectively). According to Table 1, the crystallized succinic acid of example 5, in which ethanol was used as the solvent, had higher yield, higher purity, and higher particle size uniformity than that of example 4, in which water was used as the solvent.

What is claimed is:

1. A method for enhancing uniformity of crystallized succinic acid, comprising the steps of:
   a) preparing a crystallization tank containing therein a jet-flow agitator composed of a rotating shaft and a plurality of inclined converging-tube blades driven by the rotating shaft into rotation;
   b) pouring a solvent into the crystallization tank of the step a), wherein the solvent is one selected from the group consisting of water, methanol and ethanol;
   c) adding succinic acid solids to the solvent of the step b) by weight ratio of the solvent to the succinic acid solids ranged from 2.0 to 10.0 to form a reaction solution;
   d) activating the jet-flow agitator of the step a) to have the inclined converging-tube blades thereof rotated at 50-500 rpm to cause the reaction solution of the step c) to undergo irregular fluctuations or mixing to disperse the succinic acid solids uniformly in the reaction solution;

e) setting a cooling rate of the crystallization tank to 10-35° C. per hour, and allowing the succinic acid solids of the reaction solution to undergo a crystallization and purification reaction for 1-8 hours at a reaction pressure of 5-100 lbf/in$^2$ and a reaction temperature of 0-90° C.; and f) after the crystallization and purification reaction of step e) completed, filtering out and removing the solvent from the reaction solution of the step e) to obtain solid residues, and drying the solid residues to obtain final products of high-purity succinic acids having a purity of 99.8-99.9%.

2. The method of claim 1, wherein the inclined converging-tube blades of the jet-flow agitator of the step a) are formed as inclined nozzle blades or inclined conical spring blades.

3. The method of claim 2, wherein in the step b) the ethanol is used as the solvent.

4. The method of claim 2, wherein in the step c), the weight ratio of the solvent to the succinic acid solids ranges from 2.3 to 7.0.

5. The method of claim 2, wherein in the step c), the weight ratio of the solvent to the succinic acid solids ranges from 4.0 to 7.0.

6. The method of claim 2, wherein in the step c), the weight ratio of the solvent to the succinic acid solids was equivalent to 4.

* * * * *